(12) United States Patent
Boenisch

(10) Patent No.: US 9,285,345 B2
(45) Date of Patent: Mar. 15, 2016

(54) ELECTROMAGNET INSPECTION APPARATUS WITH A MOVABLE MAGNET AND METHOD FOR NON-DESTRUCTIVE TESTING OF ELECTRICALLY CONDUCTIVE TEST COMPONENTS

(75) Inventor: Andreas Boenisch, Schwarmstedt (DE)

(73) Assignee: Innospection Group Limited (GB)

( * ) Notice: Subject to any disclaimer, the term of this patent is extended or adjusted under 35 U.S.C. 154(b) by 0 days.

(21) Appl. No.: 13/509,781

(22) PCT Filed: Nov. 12, 2010

(86) PCT No.: PCT/GB2010/051891
§ 371 (c)(1),
(2), (4) Date: Feb. 6, 2013

(87) PCT Pub. No.: WO2011/058369
PCT Pub. Date: May 19, 2011

(65) Prior Publication Data
US 2013/0127452 A1    May 23, 2013

(30) Foreign Application Priority Data
Nov. 16, 2009   (GB) .................................. 0920004.9

(51) Int. Cl.
*G01N 27/90*    (2006.01)

(52) U.S. Cl.
CPC .......... *G01N 27/904* (2013.01); *G01N 27/9033* (2013.01)

(58) Field of Classification Search
CPC ............................ G01N 27/82; G01N 27/9033
USPC .................... 324/220–221, 240–243
See application file for complete search history.

(56) References Cited

U.S. PATENT DOCUMENTS

| | | | |
|---|---|---|---|
| 3,535,624 A | * | 10/1970 | Wood .............................. 324/226 |
| 4,553,095 A | | 11/1985 | Schenk, Jr. et al. |
| 4,675,604 A | * | 6/1987 | Moyer et al. .................. 324/220 |
| 5,117,182 A | | 5/1992 | Cecco et al. |

(Continued)

FOREIGN PATENT DOCUMENTS

| | | |
|---|---|---|
| DE | 102007004223 A1 | 7/2008 |
| GB | 2245071 A | 12/1991 |

(Continued)

OTHER PUBLICATIONS

International Search Report and Written Opinion dated Mar. 24, 2011 from International Patent Application No. PCT/GB2010/051891 filed Nov. 12, 2010 (11 pages).

*Primary Examiner* — Jay Patidar
(74) *Attorney, Agent, or Firm* — Sunstone IP

(57) ABSTRACT

An inspection tool for the non-destructive testing of a test component made of an electrically conductive material is described. The inspection tool employs movably mounted permanent magnets, which provides a means for generating a variable DC magnetic field within the test component, and eddy current probes so as to provide a means for performing a partial saturation eddy current test upon the test component. The eddy current probe preferably comprises an integrated magnetic field sensor which increases the accuracy and flexibility of the modes of operation of the described apparatus and methods. The described apparatus and methods are particularly suited for the inspection of tubular components that are often remotely located within the oil and gas exploration and production industries.

23 Claims, 9 Drawing Sheets

(56) References Cited

U.S. PATENT DOCUMENTS

| | | | |
|---|---|---|---|
| 5,130,652 A | 7/1992 | Kawakami et al. | |
| 5,237,270 A * | 8/1993 | Cecco et al. | 324/220 |
| 6,037,767 A | 3/2000 | Crescenzo et al. | |
| 6,396,262 B2 * | 5/2002 | Light et al. | 324/240 |
| 6,762,602 B1 * | 7/2004 | Laursen et al. | 324/220 |
| 2002/0093343 A1 * | 7/2002 | Amini | 324/644 |
| 2003/0080735 A1 | 5/2003 | Wache | |
| 2003/0117142 A1 * | 6/2003 | Amini | 324/339 |
| 2004/0239345 A1 * | 12/2004 | Amini | 324/702 |
| 2008/0092672 A1 * | 4/2008 | Gibson et al. | 73/865.8 |
| 2008/0313915 A1 | 12/2008 | Dos Santos et al. | |
| 2010/0126278 A1 * | 5/2010 | Kubota et al. | 73/618 |
| 2011/0234212 A1 * | 9/2011 | Lepage et al. | 324/219 |

FOREIGN PATENT DOCUMENTS

| | | | |
|---|---|---|---|
| GB | 2429254 A * | 2/2007 | |
| JP | 5281198 A | 4/1992 | |
| JP | 8136509 A | 11/1994 | |
| WO | 0216184 A1 | 2/2002 | |
| WO | 2008090370 A2 | 7/2008 | |

* cited by examiner

ELECTROMAGNET INSPECTION APPARATUS WITH A MOVABLE MAGNET AND METHOD FOR NON-DESTRUCTIVE TESTING OF ELECTRICALLY CONDUCTIVE TEST COMPONENTS

The present invention relates to non-destructive testing, and in particular to a method and apparatus for the inspection of electrically conductive components. Applications of the invention include the inspection of tubular components that are often remotely located within the oil and gas exploration and production industries.

A variety of components are employed within the oil and gas industry, such as casings, production tubing, pipelines, flexible risers and steel wire ropes. In order to monitor the structural integrity of these components a variety of non-destructive testing techniques are known for the detection and identification of defects and/or fatigue in the external wall of these tubular components.

One such non-destructive testing technique known in the art is ultrasound inspection, for example as described in U.S. Pat. No. 4,162,635 or US patent publication no. US 2008/0313915. The ultrasound signal is transmitted into the tubing wall, and analysis of the signal reflected from the opposing wall allows information on the wall thickness to be derived. A number of different ultrasonic tools and methods are available, but there are drawbacks and deficiencies associated with their operation. Firstly, ultrasonic tools operating according to the contact method require good coupling between the contact transducers and the test object, and the large mismatch in the acoustic impedance of air and the acoustic impedance of the test material must be overcome. This requires the use of a couplant, for example a liquid or gel-like material that has a low acoustic impedance mismatch and therefore good acoustic coupling between the transducers and the tubular. Ultrasonic inspection tools are also highly sensitive to dirt and debris, which can interfere with the acoustic coupling and/or show up as anomalous features or artefacts in the analysed data. This means that ultrasonic inspection may not be practicable for some oil and gas exploration environments.

A second non-destructive testing technique known in the art is magnetic flux leakage testing (MFL). The basic principle is that a powerful magnetic circuit is used to magnetise the component to be tested. At areas where there is corrosion or missing metal, the magnetic field "leaks" from the component and is detected by the MFL probe. The method is therefore limited to use with ferromagnetic materials.

Typically the MFL probe consists of one of two types of magnetic pickups: a coil type or a Hall element. The coil type sensor picks up the rate of change of flux while the Hall type sensor picks up absolute magnetic field. Since the coil output is proportional to the rate of change of flux, the signal is dependent on the scanning speed. At low speeds the coils can totally miss long areas of wall loss if the changes in wall thickness are gradual. The Hall element sensor has no such restrictions.

The output of the MFL sensors is related to change of flux caused by the defect volume, but not directly by defect depth. This technique is therefore an indirect measurement of flaw size. For a proper repeatable signal it is important to magnetize the test component to a very high level (saturation). For pipe types with high wall thickness or thick coating, this is often not possible. The MFL measurement is thus limited to use with certain pipe types.

A third non-destructive testing technique known in the art is eddy current testing (ECT). ECT is based on the principle of measuring the absolute or relative impedance Z of a probe or sensor that comprises a conducting coil to which an alternating current is applied. When the alternating current is applied to the probe a magnetic field develops in and around the coil. This magnetic field expands as the alternating current rises to a maximum and collapses as the current is reduced to zero. If another electrical conductor (the apparatus to be tested) is brought into close proximity to this changing magnetic field, electromagnetic induction takes place and eddy currents (swirling or closed loops of currents that exist in metallic materials) are induced within the apparatus to be tested. The eddy currents flowing in the test material generate their own secondary magnetic fields which oppose the primary magnetic field of the coil and thus change the impedance detected by the probe. This entire process can occur from several hundred times to several million times each second depending on the frequency of the applied alternating current.

In general, the probe is initially balanced on a defect free area of the apparatus to be tested. The probe is then moved relative to the apparatus and variations in the probe impedance Z are recorded. At regions of discontinuities (defects, material property variations, surface characteristics etc) the flow of the eddy currents is distorted and hence a change of the impedance Z is measured by the probe.

For ECT techniques the probes can be configured in two different operational modes: referred to as absolute and differential modes. Absolute probes generally have a single test coil that is used to generate the eddy currents and sense changes in the eddy current field as the probe moves over the apparatus being tested. Absolute coils are generally suited for measuring slowly varying proprieties of a material. In particular they can be used for conductivity analysis, liftoff measurements, material property changes and thickness measurements.

Differential probes have two active coils usually wound in opposition. When the two coils are over a flaw-free area of test sample, there is no differential signal developed between the coils since they are both inspecting identical material. However, when one coil is over a defect and the other is over good material, a differential signal is produced. Differential probes therefore have the advantage of being very sensitive to localised defects yet relatively insensitive to slowly varying properties such as gradual dimensional or temperature variations.

ECT is an excellent method for detecting surface and near surface defects when the probable defect location and orientation is well known. However, ECT does have some inherent limitations. For example the techniques are only applicable to conductive materials; they require the surface to be tested to be accessible to the probe; and they are limited in the depth of penetration into the material being tested that can be achieved.

Partial Saturation Eddy Current Testing (PSET) is a particular type of eddy current test. PSET techniques employ conventional eddy current coils to monitor the impedance levels within a ferromagnetic material that is being tested. The eddy current coils are however located between two poles of an electromagnet and the electromagnet is arranged to apply a DC magnetic field to the material in the region being monitored by the eddy current coils. The principle behind the PSET technique is that when the ferromagnetic material is magnetised by the DC electromagnet the permeability within the material is changed. When a defect is present the magnetic field generated by the electromagnet experiences a higher flux density, analogous to the situation where a stone is placed in a river causing the water flow to divert around it. This higher flux density causes a change in the localised relative permeability and so distorts the induced eddy current fields in the material which is then detected as a change of the impedance Z measured by the probe.

PSET effectively monitors the relative change in the permeability of a material and so this technique is inherently less sensitive to gradual material property changes. It is therefore particularly effective when operated in a differential mode for the detection of localised discontinuities, such as those caused by cracks, pits and defects.

Since PSET is a relative or comparative technique, the system must be calibrated on reference samples with artificial damage and defects so as to identify the type and severity of defect. However, in practice the material of the reference sample and the test sample may be different. For example, the reference sample may have a relative permeability of 2,500 H m$^{-1}$. However the inspection pipe may have a relative permeability of 2,000 H m$^{-1}$. As a result with conventional PSET techniques the identified defect often needs to be determined or corroborated by an alternative NDT technique, for example by ultrasound testing, since the relative permeability of the pipe is usually not known. Often this is not a viable option and even when available it is time consuming and expensive.

Theoretically, PSET can also be operated within an absolute mode. However there is a known inherent problem associated with such tests. When carrying out an absolute mode PSET false hits are known to occur; i.e. a defect can be indicated when one does not truly exist. The reason for these false hits is the fact that PSET readings can be influenced by material property changes. These may include changes in electrical conductivity or changes in the grain structure, for example due to the effects of fatigue within the material. These material property changes affect the relative permeability of the material which in turn is then detected during the absolute mode PSET. The absolute mode PSET cannot however distinguish inherent material property changes from genuine problems such as wall loss. This is because the PSET does not directly measure changes in permeability, it only obtains an apparent change in permeability due the effect this has on the induced eddy currents. Thus, this apparent change could equally well be a result of a material property change or a wall loss, or indeed a combination of the two.

Theoretically, similar false readings can occur during PSET operated in a differential mode if the material property change occurs within a very localised area. However, in reality the frequency of such false readings is much lower than those described in relation to an absolute mode of operation.

The nature of the oil and gas exploration and production industry is such it is expensive and time consuming to remove or replace these components. Therefore, it is highly desirable to be able to carry out any non-destructive testing of the components while they are in situ. Furthermore, in order to obtain the best results it is vital to be able to mount the sensing apparatus as close as possible to the surface of the components to be tested. Over and above the above mentioned limitation of ultrasound testing, MFL testing, ECT and PSET these factors provide further logistical issues when deploying and operating the sensing apparatus, particularly within remote environments. For example, with MFL testing and PSET it is often necessary to locate, maintain and power heavy electromagnets in close vicinity to the components which may be located subsea.

A schematic representation of a flexible riser 1 is provided in FIG. 1. Flexible risers are an example of a component employed to transport hydrocarbons, normally from a well head or manifold on the sea-bed to a floating production platform. These components need to be flexible in order to accommodate the movement of the floating production equipment on the sea surface. They are made of several layers of steel wires that can move with respect to each other. Typically the flexible riser 1 comprises the following layers: an outer thermoplastic sheath 2; first 3a and second 3a longitudinal armament layers in this example separated by a first intermediate thermoplastic sheath 4a; a second intermediate thermoplastic sheath 4b; a radial armament layer 5 (commonly referred to as the zeta layer or zeta wire); an inner thermoplastic sheath 6 and an internal stainless steel carcass 7.

Due to the multi-layer design of the flexible riser 1, it is difficult to inspect all of the components contained therein with the non-destructive testing apparatus known in the art. Operators of flexible risers 1 are particularly concerned with the early detection of defects such as cracks, corrosion, erosion and fatigue within the different layers under various tensional stress levels. Thus, even if the previously described non-destructive inspection apparatus can be deployed with the flexible riser 1 they would only be able to inspect the layers to which they can gain physical access, with the inner layers remaining uninspected.

Furthermore, internal inspection of the flexible riser 1 by MFL testing techniques is not possible because the internal stainless steel carcass 7 comprises an unmagnetisable interlocking layer. The closest magnetisable layer would typically be located several millimeters away from the sensor. From the outside the outer thermoplastic sheath 2, typically made from polyethylene, leads to the same problem and thus flexible risers 1 demands the employment of a different inspection technology. In addition, the structure of the layers consisting of single wires wound in different directions represents a magnetic anisotropy. This means that the so-called zeta wire 5 which is responsible for the strength of the pipe against internal pressure is more difficult to magnetise as compared to a solid steel pipe wall.

One aim and object of aspects of the present invention is to provide a method and apparatus which overcomes or mitigates the drawbacks of prior art non-destructive testing techniques. A further aim and object of aspects of the invention is to provide an alternative method and apparatus to those proposed in the prior art and in particular one that is suited for deployment in situ with components located within remote environments. A further aim and object of aspects of the invention is to provide a non destructive testing method and apparatus that is suitable for use with a flexible riser. Additional aims and objects will become apparent from reading the following description.

SUMMARY OF INVENTION

According to a first aspect of the present invention there is provided an inspection tool for the non-destructive testing of a test component made of an electrically conductive material the inspection tool comprising one or more sensor modules configured to locate with a surface of the test component wherein the one or more sensor modules comprises a magnetiser unit having a movably mounted permanent magnet suitable for generating a variable DC magnetic field within the test component and at least one eddy current probe wherein the one or more sensor modules are configured to perform a partial saturation eddy current test upon the test component.

In the context of this description, the term partial saturation eddy current (PSET) refers to an eddy current testing technique in which applied magnetic field lines are used in combination with an eddy current signal. This terminology is known in the art, but may also be referred to as magnetic biased or DC field biased eddy current testing.

Employment of a moveably mounted permanent magnet for generating the variable DC magnetic field within the test component removes the requirement for heavy electromagnets to be employed so making the inspection tool lighter and easier to deploy particularly within remote environments.

The inspection tool may further comprise a clamp wherein the clamp provides a means for attaching the inspection tool to the test component.

Preferably the clamp comprises at least two pivotally attached clamp sections wherein a sensor module is mounted upon each clamp section.

Optionally the clamp further comprises one or more pair of rollers which provide a means for assisting movement of the inspection tool relative to the test component.

Preferably the one or more sensor modules further comprises a sensor that provides a means for determining the magnetic field level generated within the test component by the magnetiser unit. The sensor may be embedded within the sensor module. With this arrangement an air gap is provided between the sensor and the test component when the inspection tool is deployed.

The sensor may provide a feedback signal to the control the position of the moveably mounted permanent magnet within the magnetiser unit. Employing the sensor within a feedback loop to the moveably mounted permanent magnet allows for the magnetic field line density within the test component to be maintained even when the distance between the sensor module and the test component varies. This provides for accurate and reproducible results to be achieved on tests performed on the components, even when they exhibit a variety of physical dimensions.

Most preferably the eddy current probe comprises a magnetic field sensor that provides a means for measuring the permeability within the test component.

The incorporation of the magnetic field sensor allows the actual permeability of a material being tested to be measured and so when used in conjunction with the magnetiser unit ensures that the permeability in the test component matches that of a calibrated standard. This removes the need for alternative NDT techniques to be employed to determine or corroborate the test results obtained by the sensor module so saving on the time and costs incurred when employing the sensor module. This embodiment of the sensor module also offers greater flexibility in its modes of operation when compared with other apparatus known in the art. For example the incorporation of the magnetic field sensor provides a means for reducing the occurrence of false readings when the sensor module is operated within an absolute mode.

Alternatively the sensor comprises a mechanical or electrical sensor arranged to determine the position of the permanent magnet within the magnetiser unit.

Preferably the magnetiser unit further comprises a magnetic yoke between the poles of which is located the movably mounted permanent magnet.

It is preferable for the at least one eddy current probe to be positioned within the sensor module such that an air gap is provided between the eddy current probe and the test component when the inspection tool is deployed.

Preferably the at least one eddy current probe is located substantially centrally between the poles of the magnetic yoke. The at least one eddy current probe, or where a plurality of probes is provided, a subset of the probes may also be flexibly supported within the sensor module in order to allow them to locate as close as possible to the test component.

Most preferably the movably mounted permanent magnet comprises a permanent magnet rotatably mounted with respect to the poles of the magnetic yoke. Relative rotation of the permanent magnet and the magnetic yoke therefore provides a means for varying the DC magnetic field generated within the test component at a particular location on the surface of the test component.

The rotatable magnet will allow the magnetic field strength to be changed. In particular it will also allow switching off of the magnetisation such that there is no flux through the test component. This will switch off the attractive force between the inspection tool and the test component. It is important for the proper handling of the inspection tool that the attractive magnetic force can be switched off.

The permanent magnet may be rotatably mounted between the poles of the magnetic yoke so as to allow the permanent magnet to be moved to a deactivated position. In the deactivated position there is no, or minimal, DC magnetic field generated by the permanent magnetic within the test component.

The magnetiser unit may further comprise pole shoes, which may be attached to the poles of the magnetic yoke. Preferably the pole shoes are shaped so as to assist location of the sensor module with the component to be tested.

Preferably the one or more sensor modules further comprises a suspension mechanism that provides a means for varying the distance between the eddy current probes and the test component.

The one or more sensor modules may further comprise one or more distance sensors that provide a means for measuring the distance from the sensor module to a first electrically conductive layer of the test component. The distance sensors therefore provide a means for monitoring the thickness of an outer non-conductive material of the component.

The eddy current probes may comprise eddy current coils arranged to operate in a differential and/or an absolute configuration. The operating frequency range for the eddy current coils is preferably in the frequency range of 1 to 500 KHz.

Most preferably the magnetic field sensor comprises a Hall sensor. The Hall sensors preferably provide a means for measuring magnetic field strengths of 0.1 to 0.5 Tesla.

Preferably the inspection tool further comprises a pressure chamber suitable for housing the electrical components of the tool.

According to a second aspect of the present invention there is provided an inspection tool for the non-destructive testing of a flexible riser the inspection tool comprising one or more sensor modules configured to locate with a surface of the flexible riser wherein the one or more sensor modules comprises a magnetiser unit having a movably mounted permanent magnet suitable for generating a variable DC magnetic field within the test component and at least one eddy current probe wherein the one or more sensor modules are configured to perform a partial saturation eddy current test upon the flexible riser.

Embodiments of the second aspect of the invention may comprise preferable or optional features of the inspection tool of the first aspect the invention, or vice versa.

According to a third aspect of the present invention there is provided a method for the non-destructive testing of an electrically conductive test component, the method comprising:
- locating one or more sensor modules comprising a movably mounted permanent magnet with a surface of the test component;
- employing the movably mounted permanent magnets to generate a variable DC magnetic field within the test component;
- performing a Partial Saturation Eddy Current test upon the test component to evaluate a condition of the test component.

Employment of movably mounted permanent magnets for generating the variable DC magnetic field within the test component removes the requirement for heavy electromagnets to be employed so making the inspection tool lighter and easier to deploy particularly within remote environments.

Preferably the method further comprises the step of moving the one or more sensor modules over the surface of the test component and repeating the step of performing the Partial Saturation Eddy Current test.

Most preferably the method further comprises the steps of measuring a permeability within the electrically conductive test component.

Preferably the method further comprises the step of varying the strength of the DC magnetic field generated within the electrically conductive test component until the measured permeability corresponds to a predetermined value.

The incorporation of the step of measuring the permeability within the electrically conductive component allows the strength of the generated DC magnetic field within the electrically conductive test component to be set so that the permeability within the test component matches that of a calibrated standard. This removes the need for alternative non destructive testing techniques to be employed to determine or corroborate the test results obtained by the inspection tool so saving on the time and costs incurred when employing the described method.

Most preferably the method for the non-destructive testing of electrically conductive components further comprises the step of automatically varying the position of the permanent magnet in response to a feedback signal from the measured permeability within the electrically conductive component.

Employing a feedback signal of the measured permeability to the generated DC magnetic field allows for the magnetic field line density and hence the permeability within the component to be maintained throughout the duration of a test. This provides for accurate and reproducible results to be achieved on tests performed on the components, even when they exhibit a variety of physical dimensions.

The method may further comprise the step of varying the strength of the DC magnetic field generated within the electrically conductive test component so as to vary the depth of penetration of at which the Partial Saturation Eddy Current test may be performed upon the test component.

Optionally the step of performing the Partial Saturation Eddy Current test upon the component comprises performing an absolute mode Partial Saturation Eddy Current test. In this embodiment when the Partial Saturation Eddy Current test detects a defect a cross reference is made, with the measured permeability within the test component so as to determine whether the detected defect is a result of a material change within the test component. Employing this cross reference check reduces the occurrence of false readings of defects being detected.

Alternatively the step of performing the Partial Saturation Eddy Current test upon the component comprises performing a differential mode Partial Saturation Eddy Current test.

The method may comprise the additional step of selecting or rejecting the test component for further use according to the evaluated damage condition. Alternatively, the method may comprise the step classifying the test component according to the evaluated damage condition.

The test component may be rejected if a limit value is exceeded in the Partial Saturation Eddy Current test.

Preferably, the method further comprises the additional step of generating a report on the condition of a test component. The method may comprise the additional step of using the evaluation of the condition of a test component to generate a display to a user. The method may comprise the additional step of using the evaluation of the condition to create an image of the condition of the test component and displaying the image to a user.

According to a fourth aspect of the present invention there is provided a method for the non-destructive testing of a flexible riser, the method comprising:
    locating one or more sensors module comprising a movably mounted permanent magnet with a surface of the flexible riser;
    employing the movably mounted permanent magnet to generate a variable DC magnetic field within the flexible riser; and
    performing a Partial Saturation Eddy Current test upon a first layer of the flexible riser so as to evaluate a condition of the first layer.

The method may further comprise the step of varying the strength of the DC magnetic field generated within the flexible riser so as to vary the depth of penetration of at which the Partial Saturation Eddy Current test may be performed upon the test component.

Most preferably the method further comprises the steps of:
    varying the strength of the DC magnetic field generated within the flexible riser; and
    performing a Partial Saturation Eddy Current test upon a second layer of the flexible riser so as to evaluate a condition of the second layer.

Embodiments of the fourth aspect of the invention may comprise preferable or optional steps of the method of the third aspect of the invention or preferable or optional features of the first and second aspects of the invention, or vice versa.

According to a fifth aspect of the present invention there is provided an inspection tool for the non-destructive testing of a test component made of an electrically conductive material the inspection tool comprising one or more sensor modules configured to locate with a surface of the test component wherein the one or more sensor modules comprises a magnetiser unit having a permanent magnet movably mounted within the sensor module and which provides a means for generating a variable DC magnetic field within the test component and at least one eddy current probe wherein the variable DC magnetic field and the at least one eddy current probe are configured to perform a partial saturation eddy current test upon the test component.

Embodiments of the fifth aspect of the invention may comprise preferable or optional features of the inspection tool of the first to fourth aspects the invention, or vice versa.

According to a sixth aspect of the present invention there is provided an inspection tool for the non-destructive testing of a flexible riser the inspection tool comprising one or more sensor modules configured to locate with a surface of the flexible riser wherein the one or more sensor modules comprises a magnetiser unit having a permanent magnet movably mounted within the sensor module and which provides a means for generating a variable DC magnetic field within the test component and at least one eddy current probe wherein the variable DC magnetic field and the at least one eddy current probe are configured to perform a partial saturation eddy current test upon the flexible riser.

Embodiments of the sixth aspect of the invention may comprise preferable or optional 2, features of the inspection tool of the first to fifth aspects the invention, or vice versa.

According to a seventh aspect of the present invention there is provided a method for the non-destructive testing of an electrically conductive test component, the method comprising:

locating one or more sensor modules comprising a permanent magnet that is movably mounted therein with a surface of the test component;

employing the movably mounted permanent magnet to generate a variable DC magnetic field within the test component;

employing the variable DC magnetic field to perform a Partial Saturation Eddy Current test upon the test component so as to evaluate a condition of the test component.

Embodiments of the seventh aspect of the invention may comprise preferable or optional features of the inspection tool of the first to sixth aspects the invention, or vice versa.

According to an eighth aspect of the present invention there is provided a method for the non-destructive testing of a flexible riser, the method comprising:

locating one or more sensors module comprising a movably mounted permanent magnet with a surface of the flexible riser;

employing the movably mounted permanent magnet to generate a variable DC magnetic field within the flexible riser; and employing the variable DC magnetic field to perform a Partial Saturation Eddy Current test upon a first layer of the flexible riser so as to evaluate a condition of the first layer.

Embodiments of the eighth aspect of the invention may comprise preferable or optional features of the inspection tool of the first to seventh aspects the invention, or vice versa.

BRIEF DESCRIPTION OF DRAWINGS

Aspects and advantages of the present invention will become apparent upon reading the following detailed description and upon reference to the following drawings in which.

DETAILED DESCRIPTION

Figure 1:
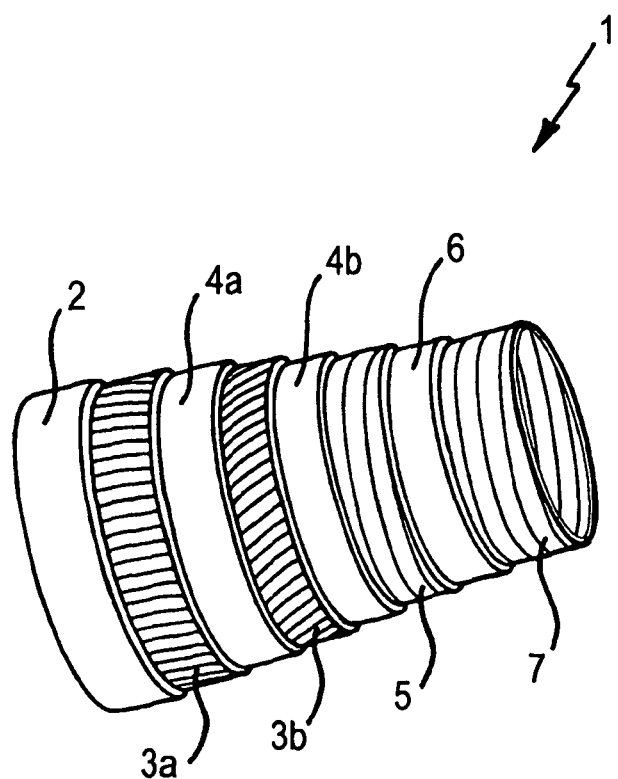
FIG. 1 presents a schematic representation of a flexible riser.

For ease of understanding the present invention will be described with reference to use with a flexible riser, a schematic representation of which is provided in FIG. 1. However, it will be appreciated by those skilled in the art that aspects of the present invention are not limited to use with such components.

Figure 2A:
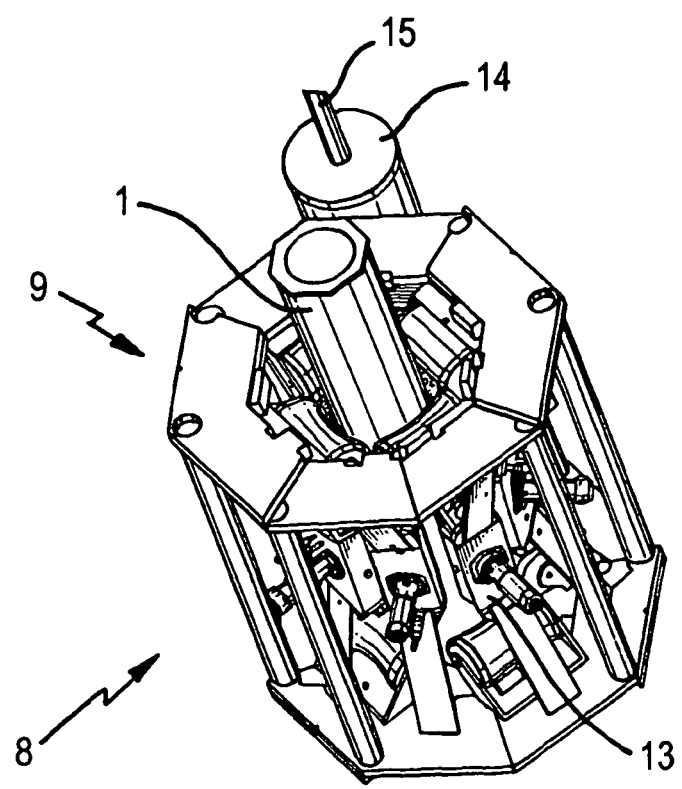
FIG. 2 presents a perspective view of an inspection tool in accordance with an embodiment of the invention within
 (a) a closed configuration;
 (b) an open configuration.
Figure 2B:
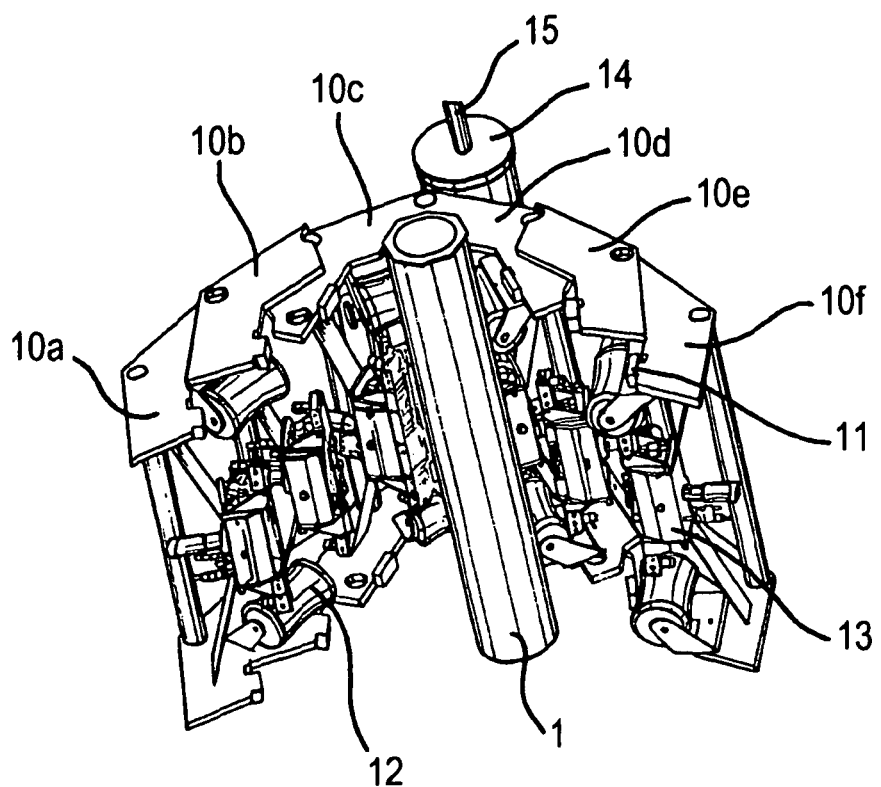

Perspective views of an inspection tool 8 in accordance with an embodiment of the present invention are provided in FIG. 2. In particular, FIG. 2(a) presents the inspection tool 8 in a closed configuration around a flexible riser 1 while FIG. 2(b) presents the inspection tool 8 in an open configuration.

The inspection tool 8 can be seen to comprise a clamp 9 that in the closed configuration of FIG. 2(a) fully encircles the flexible riser 1. The clamp 9 comprises six separate clamp sections 10 a to f that are pivotally mounted to each other. A mechanical clasp 11 provides a means for securing the first clamp section 10a to the sixth clamp section 10f when the inspection tool 8 is in its closed configuration. The clamp 9 further comprises four pairs of rollers 12 which assist the movement of the inspection tool 8 along the flexible riser 1 when a test is being carried out.

Mounted upon each clamp section 10 a to f is a sensor module 13 full details of which are described below. A pressure chamber or electronic bottle 14 is attached to the pivot located between the third clamp section 10c and the fourth clamp section 10d. Housed within the electronic bottle 14 are the various electrical components associated with the sensor modules 13, as also described in further detail below. An umbilical 15 connects the inspection tool 8 with an inspection control unit 16 that is situated on the floating production platform.

It will be appreciated that the number of clamps sections 10 a to f and associated sensor modules 13 employed within the inspection tool 8 can be varied depending on the dimensions of the component to be tested and upon the desired circumferential coverage of the component. For a flexible riser 1 it is desirable to employ sufficient sensor modules 13 so that the entire circumference of the component can be tested simultaneously. For relatively small diameter components this circumferential coverage may be achieved with as a single sensor modules 13, although typically between four and sixteen sensor modules 13 may be employed.

Figure 3:
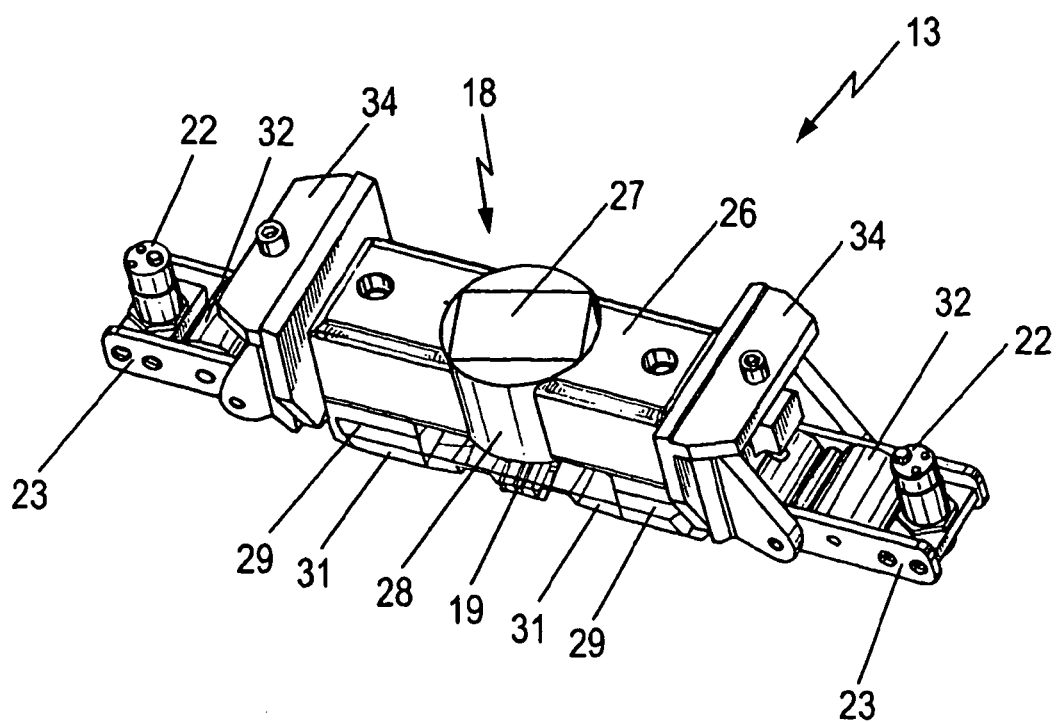
FIG. 3 presents a perspective view of a sensor module in accordance with an embodiment of the invention.
Figure 4:
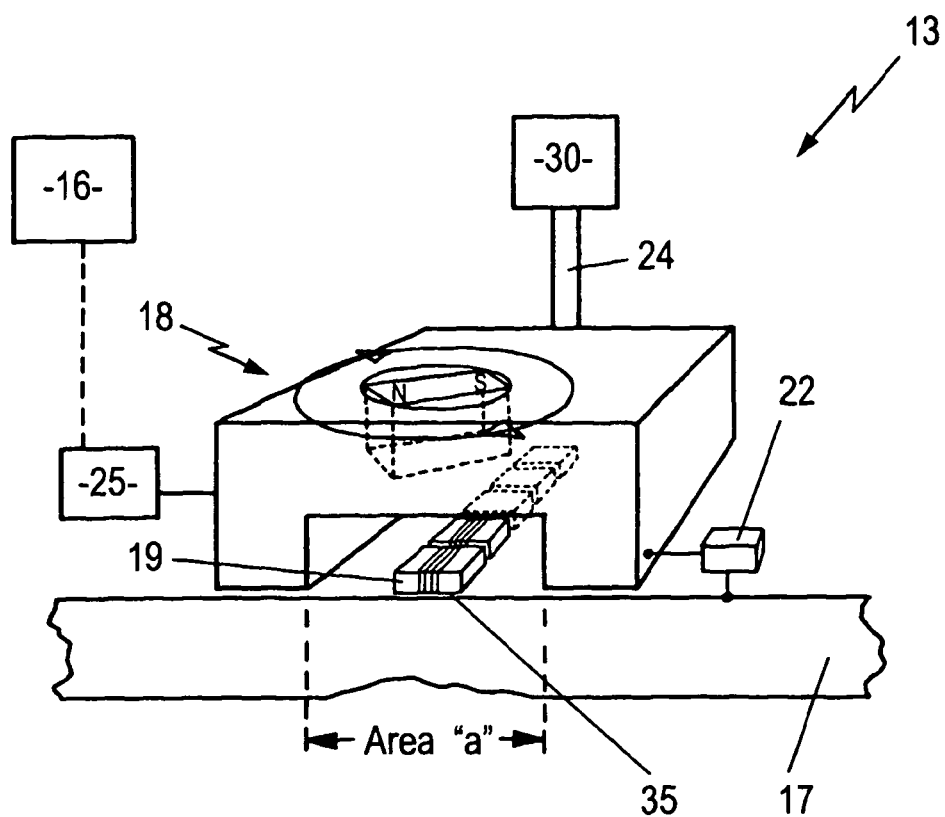
FIG. 4 presents a schematic representation of the sensor module of FIG. 3.

FIG. 3 presents a perspective view of the sensor module 13 mounted within each of the clamp sections 10 a to f, while for illustrative purposes, FIG. 4 presents a schematic representation of the sensor module 13 located with a single layer component to be tested 17. The sensor module 13 can be seen to comprise a DC magnetiser unit 18, an array of eddy current probes 19, each eddy current probe 19 comprising an eddy current coil 20 with an integrated magnetic field sensor 21 e.g. a Hall sensor, two distance sensors 22 and two suspension wheel mechanisms 23. Electronic connectors 24 are employed to provide power to the sensor module 13 e.g. for the DC magnetiser unit 18, the eddy current coils 20, the Hall sensors 21 etc.

Signals detected by the sensor module 13 are transmitted to the inspection control unit 16 via the umbilical 15 that is employed to record all of the eddy current coil 20 and Hall sensor 21 data. The control unit 16 may form an integrated part of the sensor module 13 or be located remotely as in the presently described embodiment. Transmission of the data may be via hardwiring e.g. via the umbilical 15 or a fibre optic line or by wireless transmission techniques. A multiplexer board 25 may be incorporated with the sensor module 13 so as to provide a means for multiplexing the data from all of the eddy current coils 20 and the integrated Hall sensors 21 in the array to respective channels of the inspection control unit 16. The multiplexer board 25 is preferably located within the electronic bottle 14.

The magnetiser unit 18 comprises a permanent magnetic yoke 26 through which the magnetic flux strength can be adjusted. To achieve this, the magnetiser unit 18 has a permanent magnet 27 located within a rotatable cylindrical barrel 28 that is positioned between the poles 29 of the permanent magnetic yoke 26. Controlled rotation of the cylindrical barrel 28 is provided by an electric motor 30 which is itself preferably controlled by the inspection control unit 16. The electric motor 30 is preferably located within the electronic bottle 14.

By rotating the permanent magnet 27 in the cylindrical barrel 28, the magnetic field lines can be arranged to be directed through the poles 29 (when the permanent magnet 27 lies perpendicular to the orientation of the poles 29) or to be directed parallel to the poles 29 (when the permanent magnet lies parallel to the orientation of the poles 29). Thus the magnetiser unit 18 can be moved between a fully activated position and a deactivated position, respectively.

Rotation of the permanent magnet 27 between the fully activated position and the deactivated position allows for the DC magnetic field strength generated by the magnetiser unit 18 to be varied while the position of the sensor module 13 as a whole remains fixed. During operation the position of the permanent magnet 27, and hence the strength of the magnetic field produced by the magnetiser unit 18, is controlled automatically by the motor 30 in conjunction with feedback from the Hall sensors 21 (as described in further detail below)

Located underneath the poles 29, may be fitted pole shoes 31 that are preferably shaped to locate with the component 17 to be tested. For example, the pole shoes 31 may exhibit a curved profile that assists the location of the sensor module 13 upon the outer surface of a pipe.

At either end of the magnetiser unit 18 are located the suspension wheel mechanisms 23. Each suspension wheel mechanisms 23 comprise a pair of rollers 32 mounted upon an adjustable arm 33. The suspension wheel mechanisms 23 therefore provide a means for varying the distance between the eddy current probes 19 and the test component 17. The positional adjustment is provided by means of two a lift-off adjustment mechanism 34. In the presently described embodiment the lift-off adjustment mechanism comprises a screw mechanism that allows the distance to be increased or decreased, as appropriate.

The distance sensors 22, which may be inductive or capacitive type sensors, are located on the adjustable arms 33. The distance sensors 22 provide a means for measuring the distance to the first metallic layer of the component 17 to be tested. Thus, if the component 17 comprises an outer non-conductive material e.g. polyethylene, then the distance sensors 22 provide a means for monitoring its thickness. This information provides valuable details of the outer plastic coatings e.g. polyethylene incorporated within components used in the oil and gas exploration and production industries. In addition, the measured distance to the first outer ferromagnetic layer helps determine the actual distance between the eddy current probes 19 and the test component 17. It will be appreciated by those skilled in the art that alternative embodiments of the sensor module 13 may comprise a single distance sensor 22.

The sensor module 13 is arranged such that the array of eddy current probes 19 are located centrally between the poles 29, and if present, the pole shoes 31 of the magnetiser unit 18. In a preferred embodiment the Hall sensors 21 comprising chips are embedded within the eddy current probes 19. In addition the eddy current probes 19 may be retracted from the plane defined by the poles 29 of the permanent magnetic yoke 26 and optionally flexibly supported in order to run as close as possible to the surface of the component 17 to be tested. With both of these arrangements an air gap 35 is provided between the eddy current probes 19 and the component 17 when the sensor module 13 is deployed. As a result the Hall sensors 21 provide a means for measuring magnetic field strength within the air gap 35. Measuring the axial magnetic field component within the air gap 35 allows for the determination of the magnetisation levels within the test component 17. This is because the parallel component of the magnetic field is continuous. The larger the air gap 35 however the more difficult it is to determine the magnetisation levels within the test component 17. This unique relation is such that if the Hall sensors 21 are calibrated for a certain magnetisation levels then the Hall sensors 21 allow for an operator to determine when the same level of magnetisation is reached within the test component 17.

The eddy current coils 20 may comprise a Bridge coil system operated in a differential and/or an absolute configuration or a send-receive coil system operated in a differential and/or an absolute configuration. The operating frequency range for the eddy current coils 20 is preferably in the frequency range of 1 to 500 KHz while the Hall sensors 21 preferably provide a means for measuring magnetic field strengths between 0.1-0.5 Tesla. These magnetic field strengths correspond to magnetisations levels of up to 1.6 T within the test component itself.

Operation of the Sensor Module

Figure 5:
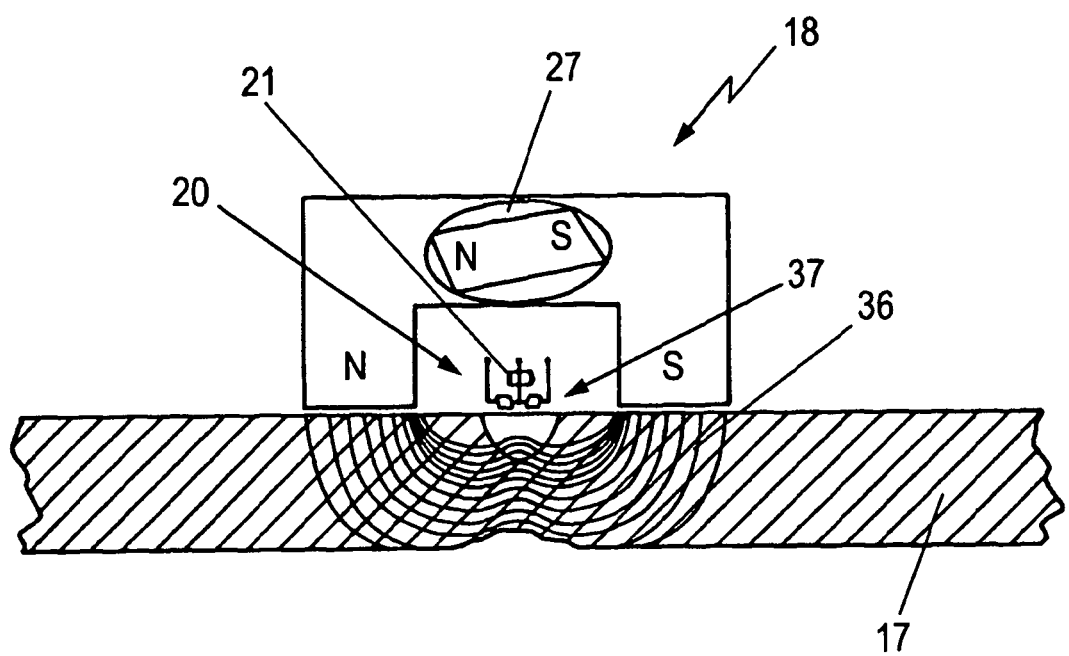
FIG. 5 presents a second schematic representation of the sensor module of FIG. 3 indicating the eddy currents and magnetic field lines present during operation.

The principles of operation of a single sensor module 13 will now be described with reference to FIG. 5. In particular, FIG. 5 shows the magnetic field line density 36 of the magnetic field generated by the magnetiser unit 18 and the eddy currents 37 generated in the test component 17 by the alternating current flowing through the eddy current coils 20. The basic steps in performing an inspection with the sensor module 13 are as follows:

employing the sensor module 13 to measure the permeability within the electrically conductive test component 17;

varying the strength of a DC magnetic field generated within the electrically conductive test component 17 until the measured permeability corresponds to a predetermined value; and performing a Partial Saturation Eddy Current test upon the test component 17 to evaluate a condition of the test component.

The first step generally employs locating the sensor module 13 at a first position upon the electrically conductive test component 17 and then selecting a frequency and strength for the AC current to drive the eddy current coils 20 so as to provide the most suitable combination for testing of the component 17. The Hall sensors 21 are then employed to measure the permeability within the electrically conductive test component 17.

The Hall sensors 21 are again employed in the step of varying the strength of the DC magnetic field generated within the electrically conductive test component 17 at the first position. Since the sensor module 13 is initially calibrated with a reference sample the Hall sensors 21 can be employed to measure the magnetic field line density 36 and, as described above, effectively provides a measurement of the permeability within this reference sample. Therefore, when the sensor module 13 is located on a defect free area of the test component 17 the DC magnetic field produced by the magnetiser unit 18 can be varied until the magnetic field line density 36, and hence the permeability within the test component 17, mirrors that used during a calibration process. Since the permeability within the calibration sample and the test component are now set to be one to one, then the influence of a defect on the eddy currents 37 will be the same. The employment of the Hall sensors 21 therefore provides a means for consistently reproducing results between the calibration sample and the test components 17. This removes the need for alternative non-destructive testing techniques to be employed to determine or corroborate the test results and so the time and costs incurred when employing the sensor module 13 to carry out a non-destructive testing is significantly reduced.

The step of performing the Partial Saturation Eddy Current test generally involves the steps of scanning can the sensor module 13 over the surface of the test component 17 so as to monitor the impedance signal detected by the eddy current coils 20 and the magnetic field strength signals detected by the Hall sensors 21. The signal detected by the eddy current coils 20 indicated the presence of defects and both signals can thereafter be analysed so as to identify the type of defects detected.

A further advantage of employing the Hall sensors 21 within the sensor module 13 is that they provide a means for maintaining the appropriate magnetic field line density 36, and hence the permeability, within the test component 17 for the duration of a scan. In reality test components 17 often comprise bends exhibiting various radii of curvature. As a result it can be difficult to maintain the thickness of the air gap 35 as the module 13 is scanned over the test component 17. Other factors which can alter the distance between the sensor module 13 and the test component 17 include variations in the thicknesses of an outer non-conductive material. If the distance between the sensor module 13 and the test component 17 increases the magnetic field line density 36 within the test component 17 will reduce. In a similar manner, if the distance between the sensor module 13 and the test component 17 decreases then the magnetic field line density 36 within the test component 17 will be increased. In order to maintain the permeability within the test component 17 the magnetic field strength needs to be increased or decreased, as appropriate.

With normal PSET apparatus it is not possible to determine the level by which the magnetic field strength should be increased or decreased. However the Hall sensors 21 provide the means for achieving this functionality since they provide a measurement of the permeability within the test component 17 and so can be employed as a feedback to the magnetiser unit 18. In this way the magnetic field line density 36 can be automatically monitored and controlled by the Hall sensors 21 and the magnetiser unit 18 so as to maintain the required level of permeability within the test component 17. Thus the sensor modules 13 can be employed with test components 17 having a variety of physical dimensions without any noticeable reduction in the accuracy of the results obtained.

A further advantage of the incorporation of the Hall sensors 21 is in their ability to reduce the occurrence of false readings, particularly within the embodiments of the sensor module 13 that employ probes comprising absolute coils. For example, consider the situation where the eddy current signal 37 detects an apparent change in permeability. As discussed previously, this apparent change in permeability may be due to wall loss or to a material changes within the test component 17. The Hall sensors 21 provide an alternative means for detecting permeability changes which result from change in the material properties itself e.g. electrical conductivity or changes in the grain structure, due to the effects of fatigue within the material. By using the results obtained from the Hall sensors 21 as a cross reference with those detected by the eddy current coils 20 those permeability changes due to inherent material changes can be eliminated during the analysis process.

Operation of the Inspection Tool

The inspection of the flexible riser 1 by the inspection tool 8 will now be described in further detail.

With the magnetiser units 18 of the sensor modules 13 located in their deactivated position the inspection tool 8 can be located around the outer surface of the flexible riser 1. Activation of the magnetiser units 18 then causes a magnetic field to be generated which assist in retaining the inspection tool 8 in the closed configuration of FIG. 2(*a*) and thus in securing it in position on the flexible riser 1.

When in the closed configuration of FIG. 2(*a*) and with the sensor module 13 activated the inspection tool 8 provides a means for carrying out a PSET over the full circumference of the flexible riser 1. It should be noted that due to the full encirclement by the magnetiser units 18, the achievable magnetization level within the ferrous (magnetisable) layers of the flexible riser 1 is significantly higher in comparison to a PSET apparatus that only covered a part of the surface of the flexible riser 1. Setting the required number of sensor modules 13 within the inspection tool 8 for a full circumferential coverage of the flexible riser 1, also ensures that all of the ferromagnetic layers within the flexible riser 1 are magnetised homogenously. This homogenous magnetization extends to all of the ferromagnetic stripes, even those that are tilted with respected to the axial orientation of the flexible riser 1.

To perform a full circumferential PSET test with the inspection tool 8 the sensor modules 13 are employed as described above. In particular, the strength of the magnetic field generated by the magnetiser units 18 is controlled so as to select which particular layer of the flexible riser 1 the eddy currents 37 are able to penetrate down into and hence which layer of the flexible riser 1 is to be inspected at that time. This is done by steadily saturating the outer layers of the flexible riser 1 with the generated magnetic fields until the layer to be inspected is reached. Once this specific layer of the flexible riser 1 is reached the magnetic field strength can be fine adjusted so as to optimise the detection of the eddy current signals 37. This process can be repeated until each of the ferrous layers of the flexible riser 1 have been tested.

The inspection tool 8 is then moved along the length of the flexible riser 1 so as to allow the PSET within each of the ferrous layers to be repeated until the whole of the flexible riser 1 has been tested. The incorporation of the suspension wheel mechanisms 23 allow for the radial position of sensor modules 13 to alter as the inspection tool 8 moves along the flexible riser 1. As a result the inspection tool 8 can negotiate bends and changes in diameter of the flexible riser 1 while allowing the sensor module 13 to remain in contact with the flexible riser 1.

The inspection tool 8 is designed such that it may operate under water. In particular the buoyancy of the inspection tool 8 is such that the net weight allows for the slow lowering of the inspection tool 8 into the water. One possible deployment method is to therefore suspend the inspection tool 8 from the surface of the water on a steel cable and allow it to slowly descend into the water and along the length of the flexible riser 1. The distance traveled by the inspection tool 8 can then be obtained from the rotation of a sheave wheel top-side. Preferably the required energy supply and detected signals would still be handled by the umbilical 15.

On completion of the test the magnetiser units 18 of the sensor modules 13 would then be located in their deactivated position again so allowing the inspection tool 8 to move to the open configuration of FIG. 2(*b*). The inspection tool 8 can therefore be detached from the flexible riser 1 and returned to the floating production platform.

Figure 6:
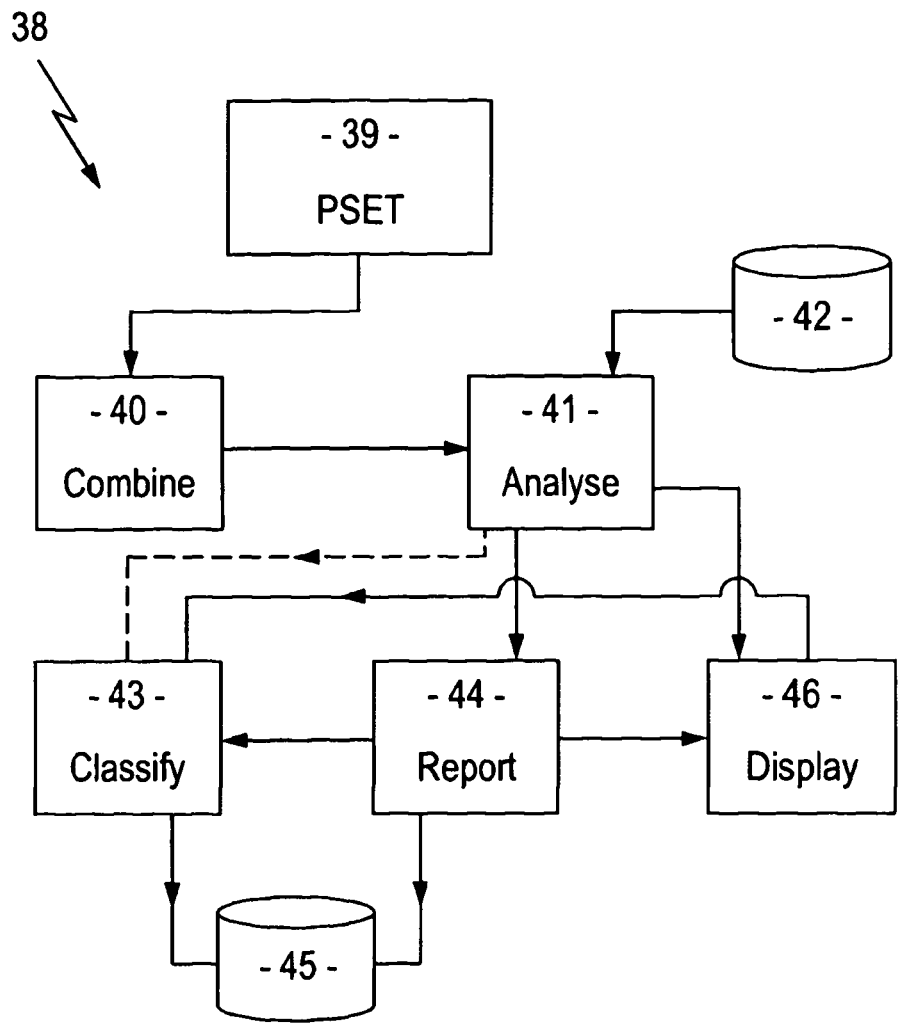
FIG. 6 presents a block diagram schematically showing the interaction of components of the apparatus of FIG. 2 in overview.

FIG. 6 shows schematically the interaction 38 of different components of the inspection tool 8. At step 39, once the Hall sensors 21 have been employed in conjunction with the magnetiser units 18 to set the required permeability within a particular layer of the flexible riser 1 the partial saturation eddy current test is performed. Test are carried out over a surface area of the flexible riser 1 and the measured data is combined at step 40 in the inspection control unit 16. At step 41, the data are analysed in the inspection control unit 16 and are compared with calibration data held in database 42. The results of this analysis may be used to directly classify (step 43) the flexible riser 1, for example indicating that it is suitable or unsuitable for a particular application. Alternatively, the classification step 43 may be based on a report at step 44. The report may be written to a database at step 45. In addition, at step 46, a display may be generated from the report, for display to a user. The user, who may be an expert in non-destructive testing and non-destructive test data interpretation, may then classify the flexible riser 1 based on their interpretation of the data. Alternatively, the expert user may confirm or verify an automatic classification performed by the inspection tool 8. The results of the classification may be stored along with the report data and details of the flexible riser 1 or particular oil and gas installation tested.

Figure 7:
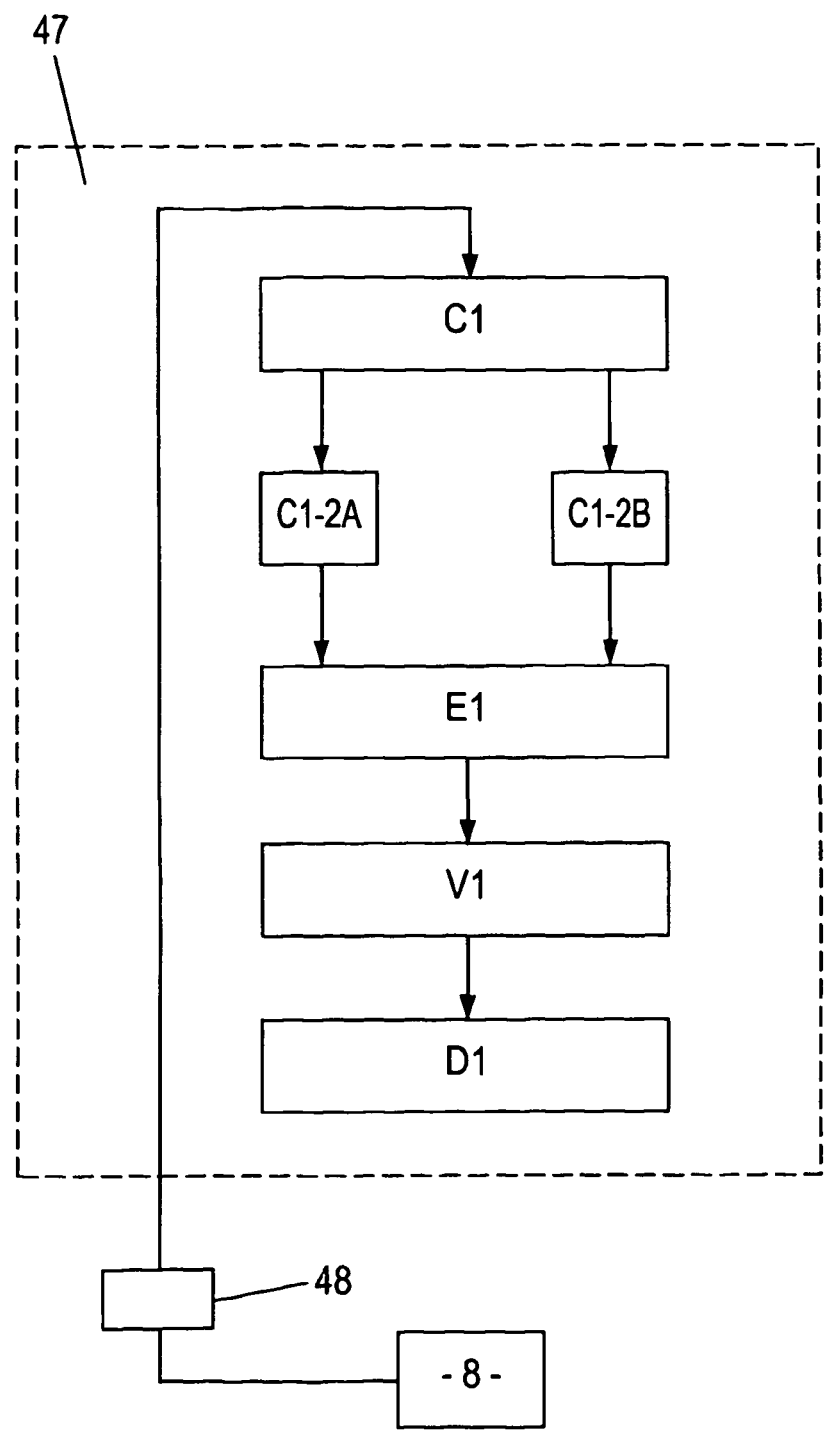
FIG. 7 is block diagram of a processing system in accordance with an embodiment of the invention.
Figure 8:
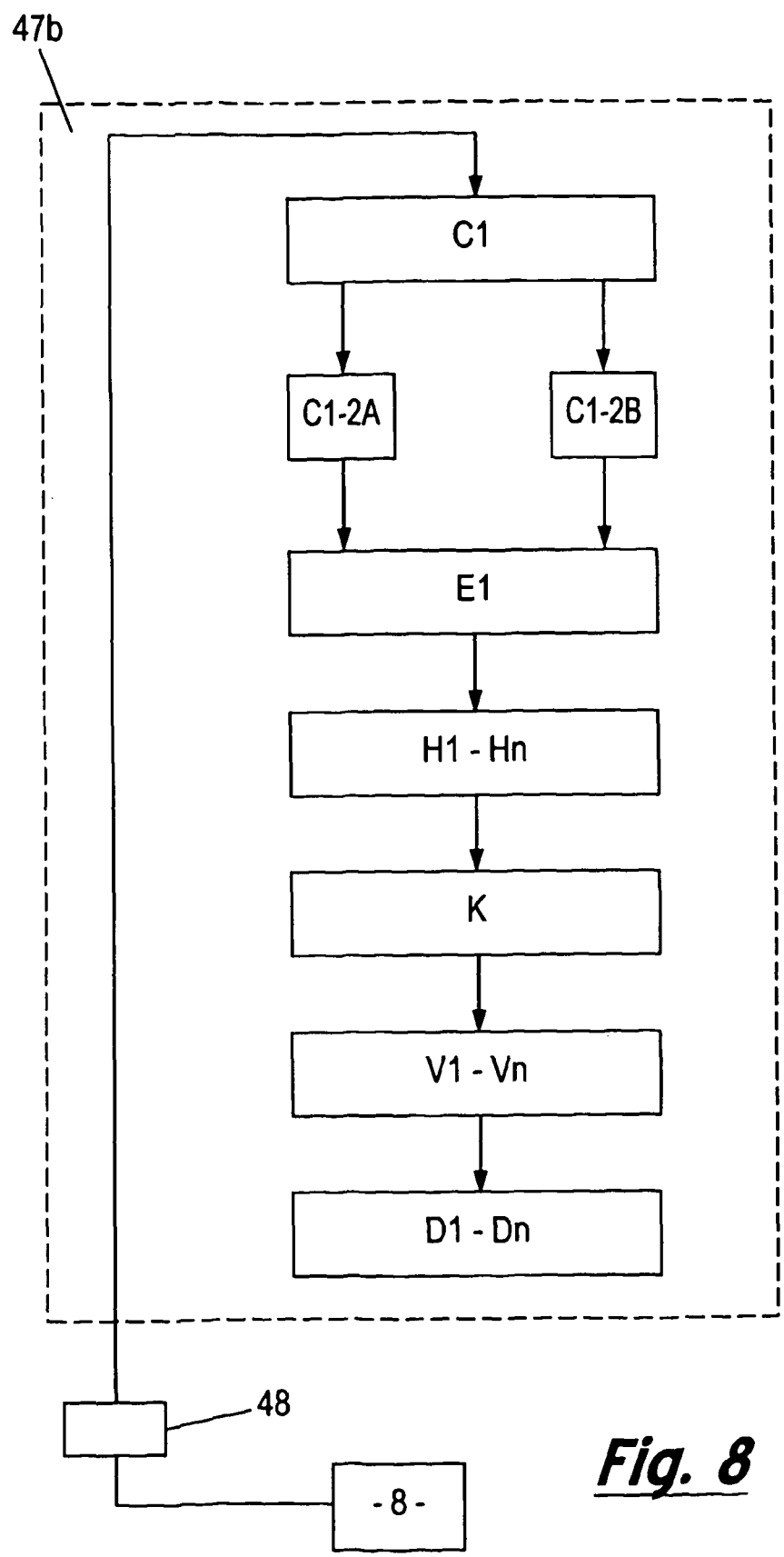
FIG. 8 is block diagram of a processing system in accordance with an alternative embodiment of the invention.

FIGS. 7 and 8 are flow charts which show the processing of the measurement data according to example embodiments of the invention. In these embodiments, the data processing module 47 is located within the inspection control unit 16 which is located remotely from the sensor modules 13, and is configured to receive the data transmitted by the sensor modules 13 via a fibre optic interface 48. The fibre optic interface 48 is preferably located within the electronic bottle 14.

In the example of FIG. 7, the measurement data are received in the data processing module 47 from the fibre optic interface 48 and multiplexer board 25. In step C1 the partial saturation eddy current measurement data are received in the data processing module 47, and the signal phase (step C1-2A) and the signal amplitude (step C1-2B) are evaluated individually. The analysing algorithm uses in step C1-2A the signal phase to characterise a type of event which has been detected in the wall of the component 17, and uses in step C1-2B signal amplitude as a representation of the order of magnitude of a detected event. The results are indicated at evaluation step E1.

This comparison with calibration data held in database 42 takes place at step V1, and may be used directly to provide an assessment of the condition of the flexible riser 1. The result of the comparison is recorded in data storage means at step D1.

An alternative processing method is shown schematically in FIG. 8 of the drawings, and is also carried out while using the sensor module 13 in data processing module 47b. The embodiment of FIG. 8 is similar to that of FIG. 7, with like steps indicated with like reference numerals. However, the embodiment of FIG. 8 differs in that provision is made for an additional evaluation of the test component 17 by the use of predetermined quality criteria which are preset into the system as analysis thresholds. An appropriate number of analysis thresholds S1 to Sn are preset in the data processing module 47b. At step H1 to Hn, the evaluation results E1 are compared with the analysis thresholds. A signal indication is output at step K, for example if the analysis threshold has been exceeded, and indicates that the test object should be rejected. In step V1-Vn, a visual indication is presented to an operator, and step D1 to Dn, the analysis results are recorded in the data storage module 45. In this embodiment, the results of the evaluation steps E1 may optionally be visually (and/or audibly) presented to the operator at steps V1-Vn.

In the method of FIG. 8, the inspection tool is calibrated before use, by using calibrating test objects. These calibrating test objects are of substantially the same dimensions and materials as the components to be inspected. The calibration test objects comprise artificially-produced instances of damage to the material with known dimensions. In a preferred embodiment, the calibration defects are made according to international standards, such as the specifications of the American Petroleum Institute (API). The test defects may for example be produced by spark erosion, machining or drilling. By using calibrated test objects, the sensitivity of the tool system to the kind of defects which are typically encountered can be verified. After calibration to the API standards, the inspection tool may be used for the inspection of components, including tubular components used in the oil and gas exploration and production industries.

In an alternative embodiment of the inspection tool 8 there may be incorporated, in addition to, or as an alternative to the Hall sensors 21, a mechanical or electrical sensor configured to monitor the rotational position of the permanent magnet 27 e.g. a potentiometer whose output varies in response to the rotational position of the permanent magnet 27. In this way the mechanical or electrical sensor may be used to determine the level of the magnetic field generated by the magnetiser units 18.

The described inspection tool provides a number of significant advantages over the apparatus and methods known in the art. In the first instance the use of a rotatable permanent magnet to provide the required magnetic field for the PSET removes the requirement for heavy electromagnets to be employed. This removes the requirement to supply considerable electrical power to the inspection tool. This has obvious benefits since the tool is often deployed in a remote sub-sea environment where the supply of power is restricted. Moreover, in generating the magnetic field no heat is dissipated which can, if not properly taken care of, destroy parts of the inspection tool.

The described inspection tool operates by employing a magnetically biased eddy current technology which is capable of carrying out non-destructive testing within various layers of a multilayer component e.g. a flexible riser. The control of the level of magnetisation allows for differentiation of which of the layers the observed defects are found located. As a result defects can be detected within deeper layers even when the layers on the top are intact.

The described sensor module provides further advantages to the inspection tool over the apparatus and methods known in the art. In the first instance the incorporation of the Hall sensors provides non-destructive test apparatus that is more accurate and flexible in its modes of operation since their employment provide a means for the actual permeability of a material being tested to be measured. As a result the Hall sensors can be used in conjunction with the magnetiser units so as to ensure that the permeability in a test component matches that of the calibrated standard. This removes the need for alternative non-destructive testing techniques to be employed to determine or corroborate the test results obtained by the inspection tool so saving on the time and costs incurred when employing the described apparatus. Indeed, as described previously, there are often environments where such alternative non-destructive test apparatus cannot be deployed and so in these circumstances determination or corroboration would simply not be available.

The Hall sensors may be employed within a feedback loop to the magnetiser units so allowing for the magnetic field line density within a test component to be maintained even when the distance between the sensor module and the test component is altered e.g. by variations in diameters of, or the presence of bends in the test component. This provides for more accurate and reproducible results on the test components, even when they exhibit a variety of physical dimensions, when compared with results obtained from non-destructive test apparatus known in the art.

The described inspection tool also offers greater flexibility in its modes of operation when compared with other apparatus known in the art. For example the incorporation of the Hall sensors provides a means for reducing the occurrence of false readings when the associated sensor modules are operated within an absolute mode. Thus the described apparatus and methods can be accurately employed in both absolute and differential mode of operation. The described apparatus and methods may therefore be readily deployed for the non-destructive testing of ferromagnetic materials in the form of single or multiple layer structures e.g. pipes, plates, vessels (tank floors, vessel plating), steel bridge structures, flexible risers and steel wire ropes (including power wires).

For single layer materials and/or structures, the inspection tool can detects and analyse the severity of defects or material property changes on the material surface, on the underside of the material as well as in the complete wall. For multiple layers materials and/or structures, the inspection tool can detect and analyse the severity of defects or material property changes in all ferromagnetic layers contained therein.

The invention provides an inspection tool for the non-destructive testing of a test component made of an electrically conductive material, and in particular for an in situ component such as a flexible riser. The inspection tool has one or more sensor modules configured to locate with a surface of the test component. The sensor modules include a magnetiser unit having a movably mounted permanent magnet, which is configured to generate a variable DC magnetic field within the test component at any fixed position along the length of the test component. At least one eddy current probe is provided and the sensor modules are configured to perform a partial saturation eddy current test within the test component.

An inspection tool for the non-destructive testing of a test component made of an electrically conductive material is described. The inspection tool employs movably mounted permanent magnets, which provides a means for generating a variable DC magnetic field within the test component, and eddy current probes so as to provide a means for performing a partial saturation eddy current test upon the test component. The eddy current probe preferably comprises an integrated magnetic field sensor which increases the accuracy and flexibility of the modes of operation of the described apparatus and methods. The described apparatus and methods are particularly suited for the inspection of tubular components that are often remotely located within the oil and gas exploration and production industries.

The foregoing description of the invention has been presented for purposes of illustration and description and is not intended to be exhaustive or to limit the invention to the precise form disclosed. The described embodiments were chosen and described in order to best explain the principles of the invention and its practical application to thereby enable others skilled in the art to best utilise the invention in various embodiments and with various modifications as are suited to the particular use contemplated. Therefore, further modifications or improvements may be incorporated without departing from the scope of the invention as defined by the appended claims.

The invention claimed is:

1. An inspection tool for the non-destructive testing of a test component made of an electrically conductive material the inspection tool comprising one or more partial saturation eddy current sensor modules configured to locate with a surface of the test component, the one or more partial saturation eddy current sensor modules comprising at least one eddy current probe and a magnetiser unit wherein the magnetiser unit comprises a permanent magnet movably mounted within the magnetiser unit to provide a means for generating a variable DC magnetic field, wherein the inspection tool further comprises a clamp for attaching the inspection tool to an outer surface of the test component.

2. An inspection tool as claimed in claim 1 wherein the clamp comprises at least two pivotally attached clamp sections wherein a partial saturation eddy current sensor module is mounted upon each clamp section.

3. An inspection tool as claimed in claim 1 wherein the clamp further comprises one or more pair of rollers which provide a means for assisting movement of the inspection tool relative to the test component.

4. An inspection tool as claimed in claim 1 wherein the one or more partial saturation eddy current sensor modules further comprises a sensor that provides a means for determining the magnetic field level generated within the test component by the magnetiser unit.

5. An inspection tool as claimed in claim 4 wherein the sensor is imbedded within the partial saturation eddy current sensor module.

6. An inspection tool as claimed in claim 4 wherein the sensor provides a feedback signal to control the position of the moveably mounted permanent magnet within the magnetiser unit.

7. An inspection tool as claimed in claim 4 wherein the sensor comprises a magnetic field sensor that provides a means for measuring the permeability within the test component.

8. An inspection tool as claimed in claim 7 wherein the magnetic field sensor comprises a Hall sensor.

9. An inspection tool as claimed claim 4 wherein the sensor comprises a mechanical or electrical sensor arranged to determine the position of the permanent magnet within the magnetiser unit.

10. An inspection tool as claimed in claim 1 wherein the magnetiser unit further comprises a magnetic yoke between a set of poles of which is located the movably mounted permanent magnet.

11. An inspection tool as claimed in claim 10 wherein the at least one eddy current probe is located substantially centrally between the poles of the magnetic yoke.

12. An inspection tool as claimed in claim 10 wherein the movably mounted permanent magnet comprises a permanent magnet rotatably mounted with respect to the poles of the magnetic yoke.

13. An inspection tool as claimed in claim 12 wherein the permanent magnet is rotatably mounted between the poles of the magnetic yoke so as to allow the permanent magnet to be moved to a deactivated position.

14. An inspection tool as claimed in claim 10 wherein the magnetiser unit further comprises pole shoes attached to the poles of the magnetic yoke.

15. An inspection tool as claimed in claim 14 wherein the pole shoes are shaped so as to assist location of the partial saturation eddy current sensor module with the component to be tested.

16. An inspection tool as claimed in claim 1 wherein the at least one eddy current probe is positioned within the partial saturation eddy current sensor module such that an air gap is provided between the eddy current probe and the test component when the inspection tool is deployed.

17. An inspection tool as claimed in claim 1 wherein the at least one eddy current probe are flexibly supported within the partial saturation eddy current sensor module in order to allow them to locate as close as possible to the test component.

18. An inspection tool as claimed in claim 1 wherein the one or more partial saturation eddy current sensor modules further comprises a suspension mechanism that provides a means for varying the distance between the eddy current probes and the test component.

19. An inspection tool as claimed in claim 1 wherein the one or more partial saturation eddy current sensor modules further comprise one or more distance sensors that provide a means for measuring the distance from the partial saturation eddy current sensor module to a first electrically conductive layer of the test component.

20. An inspection tool as claimed in claim 1 wherein the eddy current probes comprise eddy current coils arranged to operate in a differential configuration.

21. An inspection tool as claimed in claim 1 wherein the eddy current probes comprise eddy current coils arranged to operate in an absolute configuration.

22. An inspection tool as claimed in claim 1 wherein the inspection tool further comprises a pressure chamber suitable for housing one or more electrical components of the tool.

23. An inspection tool for the non-destructive testing of a flexible riser the inspection tool comprising one or more partial saturation eddy current sensor modules configured to locate with a surface of the flexible riser, the one or more partial saturation eddy current sensor modules comprising at least one eddy current probe and a magnetiser unit wherein the magnetiser unit comprises a permanent magnet movably mounted within the magnetiser unit to provide a means for generating a variable DC magnetic field, wherein the inspection tool further comprises a clamp for attaching the inspection tool to an outer surface of a test component.

* * * * *